United States Patent
Bowen et al.

(10) Patent No.: US 10,858,722 B2
(45) Date of Patent: Dec. 8, 2020

(54) PLATINUM-NICKEL-BASED ALLOYS, PRODUCTS, AND METHODS OF MAKING AND USING SAME

(71) Applicant: Deringer-Ney Inc., Bloomfield, CT (US)

(72) Inventors: Patrick Bowen, Windsor, CT (US); Edward Smith, Madison, CT (US)

(73) Assignee: Deringer-Ney, Inc., Bloomfield, CT (US)

( * ) Notice: Subject to any disclaimer, the term of this patent is extended or adjusted under 35 U.S.C. 154(b) by 188 days.

(21) Appl. No.: 16/137,988

(22) Filed: Sep. 21, 2018

(65) Prior Publication Data

US 2020/0095653 A1    Mar. 26, 2020

(51) Int. Cl.
| | | |
|---|---|---|
| *C22C 5/04* | (2006.01) | |
| *C22F 1/14* | (2006.01) | |
| *G01R 1/067* | (2006.01) | |
| *F16F 1/04* | (2006.01) | |
| *F16F 1/02* | (2006.01) | |
| *G01R 1/073* | (2006.01) | |

(52) U.S. Cl.
CPC ............. *C22C 5/04* (2013.01); *C22F 1/14* (2013.01); *F16F 1/021* (2013.01); *F16F 1/04* (2013.01); *G01R 1/06755* (2013.01); *F16F 2224/0208* (2013.01); *F16F 2226/02* (2013.01); *G01R 1/07342* (2013.01)

(58) Field of Classification Search
CPC ............. C22C 5/04; C21F 1/14; C22F 1/14
See application file for complete search history.

(56) References Cited

U.S. PATENT DOCUMENTS

| | | | |
|---|---|---|---|
| 2,361,578 | A | 10/1944 | Vilensky |
| 8,183,877 | B2 | 5/2012 | Tanaka |
| 9,234,262 | B2 | 1/2016 | Klein et al. |
| 2003/0018380 | A1 | 1/2003 | Craig et al. |
| 2006/0197542 | A1 | 9/2006 | Tanaka |

FOREIGN PATENT DOCUMENTS

KR    100718577 B1    5/2007

OTHER PUBLICATIONS

"Glossary of Metallurgical Terms and Engineering Tables", In ASM Metals Handbook: Desk Edition. Metals Park, OH: American Society for Metals, 1985.
Cowley, Alison et al., "A Healthy Future: Platinum in Medical Applications Platinum Metals Rev 55 (2): 98-107", https://doi.org/10.1595/147106711X566816, 2011, 10 pages.
Dahmani, C. E. et al., "Temperature Dependences of Atomic Order Relaxations in Ni—Pt and Co—Pt Alloys", Acta Metallurgica 33 (3): 369-77. https://doi.org/10.1016/0001-6160(85)90079-3, 1985.
Greenberg, B. A. et al., "Optimised Mechanical Properties of Ordered Noble Metal Alloys I. Preliminary Strong Cold Deformation Results in Optimised Mechanical Properties", Platinum Metals Review 47 (2): 46, 2003.
Greenholz, M A. et al., "Kinetics of Ordering in NiPt", Journal of Materials Science 7 (11): 1285-1291, 1972.
Guo, J L. et al., "Platinum Alloy Strain Gauge Materials: Noble Metal Alloys for Static Strain Measurement at 900°C", Platinum Metals Rev 41 (1): 24, 1997.
Hannah, R L. et al., "Strain Gage Users' Handbook", https://www.springer.com/us/book/9780412537202, 1992.
Li, Bernard et al., "Fatigue Performance and Microstructure of Pt-20Ir Wire and Its Coil for Medical Device Application", In ICMFF10, 2013.
Tong, L. et al., "Noble Metal Alloys as Strain Gauge Materials: Their Development for High Temperature Applications", Platinum Metals Rev 38 (3): 98-108, 1994.
Wang, D. et al., "Structurally Ordered Intermetallic Platinum—cobalt Core—shell Nanoparticles with Enhanced Activity and Stability as Oxygen Reduction Electrocatalysts", Nature Materials 12 (1): 81-87. https://doi.org/10.1038/nmat3458, 2013.
International Search Report and Written Opinion issued in PCT Application No. PCT/US2019/052176, dated Dec. 30, 2019, 10 pages.

*Primary Examiner* — Jessee R Roe
(74) *Attorney, Agent, or Firm* — Dorsey & Whitney LLP

(57) ABSTRACT

Platinum-nickel-based ternary or higher alloys include platinum at about 65-80 wt. %, nickel at about 18-27 wt. %, and about 2-8 wt. % of ternary or higher additions that may include one or more of Ir, Pd, Rh, Ru, Nb, Mo, Re, W, and/or Ta. These alloys are age-hardenable, provide hardness greater than 580 Knoop, ultimate tensile strength in excess of 320 ksi, and elongation to failure of at least 1.5%. The alloys may be used in static and moveable electrical contact and probe applications. The alloys may also be used in medical devices.

24 Claims, 11 Drawing Sheets

PLATINUM-NICKEL-BASED ALLOYS, PRODUCTS, AND METHODS OF MAKING AND USING SAME

TECHNICAL FIELD

The present disclosure relates to compositions of alloys of platinum, probes and wires comprising the platinum alloy compositions, microcoils comprising the platinum alloy compositions, methods of making the same, and methods of using the same for instance in medical and electronic applications.

BACKGROUND

Alloys in Medical Applications:

Tips are a relatively high complexity portion of the guidewire assemblies employed in percutaneous coronary intervention. To balance the need in these devices to combine radiopacity with high rotational stiffness and bending flexibility, the tapered wire core is often terminated about 1 in. from the distal end of the guidewire and transitioned into a coiled precious metal wire.

Prior art largely avoids mentioning which specific metal alloy compositions are used specifically to form the microcoils used in guidewire tips. Widely available metallic materials known to be consistent with the aforementioned application criteria for use as catheter guidewire tip microcoils may include:

1). 89.5 wt. % Pt-10.5 wt. % Ni (Cowley and Woodward 2011),
2). 90 wt. % Pt-10 wt. % Ir and 80 wt. % Pt-20 wt. % Ir (Li, Zhang, and Cho 2013),
3). 92 wt. % Pt-8 wt. % W (Cowley and Woodward 2011), and
4). Paliney® 1100 or "Pd—Re" (Klein and Smith III 2008)

For application in intravascular or implantable medical devices, US 2003/0018380 A1 (Craig et al. 2003) discloses an alloy of 2-50% Pt by weight, with additional constituents of Ni from 5 to 12%, Cr from 11 to 18%, and Fe. One application for this material is the production of strip, wire, or tube (cannula) that is then formed into an endovascular prosthesis (i.e., stent). 316 L and similar grades of stainless steel is a standard material for endovascular prosthesis construction.

Alloys in Probe Applications:

In the evaluation of electronic devices, a test tool is connected to test points on the device under scrutiny using a multitude of small metallic objects called "probes" or "pins." Probes may take the form of cantilever probes, cobra probes, vertical probes, pogo probe assembly components, and so forth. Probes are often arranged into arrays with fixed positions matching the test points, called the "probe card."

There also exist test probes of larger cross-section, where the same wear resistance and nobility as found in the smaller probes is desired. In these cases, a solid noble metal alloy construction becomes prohibitively expensive. In these applications, the noble metal alloy of the present disclosure may be attached to a non-precious metal alloy "shaft," thereby forming a probe having the electrical contact characteristics of a solid noble metal alloy, but at a reduced cost.

In U.S. Pat. No. 8,183,877 B2 (Tanaka 2012), probe materials based on Pt are disclosed. Various compositions of binary Pt alloys containing Ni, W, Ir, and/or Co are disclosed at platinum contents ranging from 70-95 wt. %. The patent discloses a binary alloy of Pt and Ni, with Ni comprising 20-30% of the alloy by weight, of a Vickers microhardness (HV) between 300 and 600. This patent also discloses other materials of the binary system Ir—Rh. It is specifically noted that "excessively hard" material above HV 600 becomes difficult to process in all binary material systems disclosed. For purposes of comparison, the *ASM Metals Handbook Desk Edition* ("Glossary of Metallurgical Terms and Engineering Tables" 1985) shows that the claimed hardness range HV 300-600 is approximately equivalent to a range of ultimate tensile strengths 138-303 ksi. While probes with the aforementioned hardness range are disclosed by U.S. Pat. No. 8,183,877 B2 (Tanaka 2012), it should be noted that the reference's embodiments of platinum-nickel alloys are only reported to achieve hardnesses of HV 300-500. All of the aforementioned platinum alloy compositions appear only to be wrought hardenable, with no teachings related to age hardenability.

In other applications, fine metal alloy films and wires comprising platinum, nickel, and other constituents are known to function as sensing elements in strain gage assemblies. The *Strain Gage Users' Handbook* discusses the application of platinum alloy filaments of various compositions (Hannah and Reed 1992). While the referenced alloys contain both platinum and nickel, nickel is present in binary alloys at low levels <10 wt. %. Tungsten is also referenced separately as an alloying addition to platinum at levels <10 wt. %. Tong, Guo, and Chen have reported in two separate contributions to *Platinum Metals Review* platinum-based materials for strain gage filaments (Tong and Guo 1994; Guo, Tong, and Chen 1997). These include alloys comprising up to six constituents. Among these include various alloys of platinum with <10 wt. % Ni, 7.5-27 wt. % W, <7% Re, <1 wt. % Cr, <0.2% Y, 45% Pd, 10% Mo, and/or 20% Ir. The aforementioned platinum alloy compositions are wrought hardenable only, and prior disclosures do not teach age hardenability of any of these strain gage materials.

In another example, an alloy of Pt and Ni was referenced in U.S. Pat. No. 2,361,578A (Vilensky 1944) for a glass working apparatus, in addition to the claimed compositional range of 0.25-2 wt. % Ni in Pt. The patent refers to poor workability of Pt—Ni at compositions above about 5 wt. % Ni, stating that the alloy becomes brittle and cannot be deformed in the cold condition. It is therefore surprising to find ranges of Ni content substantially above this level that retains workability at room temperature.

SUMMARY

The approaches previously discussed illustrate that nickel in platinum is employed most commonly at levels <12 wt. %, and that additions in excess of that are conventionally associated with reduced processability. Platinum alloys with nickel in excess of this level are limited. Of those higher-level additions, materials with hardness level of HV 600 are considered to be undesirable.

According to certain implementations, a platinum and nickel-based ternary or higher alloy is provided that can be age hardened to an ultimate tensile strength of at least 320 ksi or at least $HK_{50}$ 600. The alloy includes platinum at about 65 to about 80 wt. % of the alloy; nickel at about 18 to about 27 wt. % of the alloy; and a ternary or higher addition totaling about 2 to about 8 wt. % of the alloy, where the ternary or higher additions comprise one or more of Ir, Pd, Rh, Ru, Nb, Mo, Re, W, Ta, or any combination thereof.

In variations and alternatives, nickel is present at about 19 to about 25 wt. % of the alloy, and the total ternary or higher additions is present at about 2 to about 7 wt. % of the alloy.

In others, the platinum is present at about 73 to about 80 wt. % of the alloy, the nickel is present at about 18 to about 24 wt. % of the alloy, and the total ternary or higher addition is present at about 2 to about 7 wt. % of the alloy. In addition or alternatively, the platinum is present at about 68 to about 73 wt. % of the alloy, the nickel is present at about 21 to about 26 wt. % of the alloy, and the ternary or higher additions are present at about 2 to about 7 wt. % of the alloy. The alloy may be substantially free of Ti, V, Cr, Mn, Fe, Co, Cu, and/or Zn. The alloy may include scandium, yttrium, or lanthanide series elements in amounts of 0.1 wt. % or less. The alloy may be annealed to a straightness of better than about 0.030 in. curvature per linear inch of length of wire and maintains an ultimate tensile strength of about 240 ksi or greater. In addition or alternatively, the alloy may be age hardened and have a microhardness of at least 580 Knoop, and/or may have an ultimate tensile strength of at least 320 ksi, and/or may have a total tensile elongation of greater than 1.5%.

Implementations also provide a spring, coil, or microcoil product may comprise a platinum-nickel-based ternary or higher alloy, where the alloy includes platinum at about 65 to about 80 wt. % of the alloy; nickel at about 18 to about 27 wt. % of the alloy; and a ternary or higher addition totaling about 2 to about 8 wt. % of the alloy, where the ternary or higher additions comprise one or more of Ir, Pd, Rh, Ru, Nb, Mo, Re, W, Ta, or any combination thereof. In such implementations, the spring, coil, or microcoil may be subjected to X-ray radiation at energies of about 40 to about 80 kV and used to produce an image in a medical setting. The alloy may have a total tensile elongation of greater than 1.5% and/or a 0.2% offset yield strength of greater than 175 ksi. The product may be a component of a guidewire comprising a core and/or tip utilizing the product.

Further implementations provide a test probe with a platinum-nickel-based ternary or higher alloy in which the alloy includes platinum at about 65 to about 80 wt. % of the alloy; nickel at about 18 to about 27 wt. % of the alloy; and a ternary or higher addition totaling about 2 to about 8 wt. % of the alloy, where the ternary or higher additions comprise one or more of Ir, Pd, Rh, Ru, Nb, Mo, Re, W, Ta, or any combination thereof.

In variations and alternatives, the probe may be configured as a cobra probe, a cantilever probe, a pogo pin probe, a vertical probe, or a MEMS probe. The alloy may be age hardened and has a microhardness of at least 600 Vickers and/or may have a tensile strength of at least 320 ksi and/or may have a total tensile elongation of greater than 1.5%.

In variations and alternatives, a probe card comprising the test probe with the platinum-nickel-based ternary or higher alloy may be provided. A probe tip may be constructed of the platinum-nickel-based ternary or higher alloy and attached to a body comprising a dissimilar metal. The probe tip may be included on a probe card.

According to other implementations, a method of producing a platinum and nickel-based ternary or higher alloy involves forming an alloy including platinum at about 65 to about 80 wt. % of the alloy; nickel at about 18 to about 27 wt. % of the alloy; and a ternary or higher addition totaling about 2 to about 8 wt. % of the alloy, where the ternary or higher additions comprise one or more of Ir, Pd, Rh, Ru, Nb, Mo, Re, W, Ta, or any combination thereof. The alloy is annealed, the annealed alloy formed into a probe tip, a spring, a coil, or a microcoil, and the formed alloy age hardened for a maximum of 8 hours, where the alloy can be age hardened to an ultimate tensile strength of at least 320 ksi or at least $HK_{50}$ 600.

DETAILED DESCRIPTION

Figure 1:
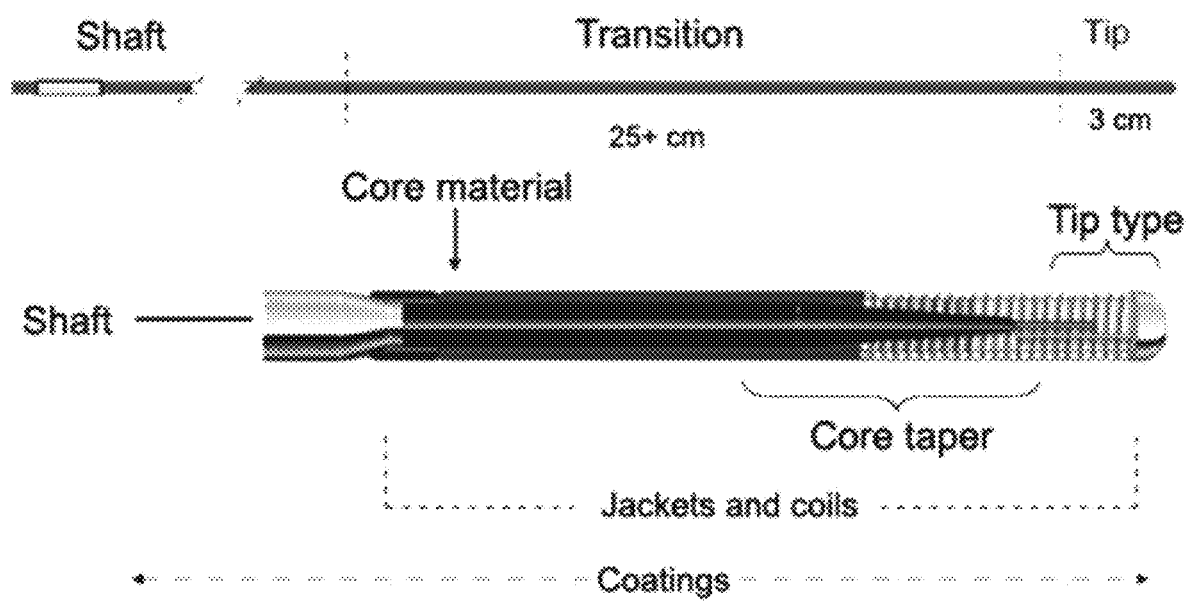
FIG. 1 is an illustration of a catheter guidewire, which, at its distal tip, may contain a microcoil formed of an alloy of the present disclosure. Image adapted from Buller et al. (2013).

The Pt—Ni—X compositions and articles of the present disclosure are workable and formable at high levels of nickel. The compositions also routinely achieve mechanical properties with ultimate tensile strengths >303 ksi, equivalent to a high hardness level of 600 Vickers. However, the alloys are still surprisingly cold workable at strip thicknesses or wire diameters below 50 μm (0.002 inches). Implementations can provide Pt—Ni-based ternary and higher order alloys, e.g., Pt—Ni—X, Pt—Ni—$X_1$—$X_2$ quaternary alloys, and so forth.

In some implementations, the Pt—Ni—X alloy may contain Pt at about 65 to about 80 wt % of the alloy, at about 73 to about 80 wt. % of the alloy, at about 68 to about 73 wt. % of the alloy, or any integer value range spanning 65 to 80 wt % of the alloy.

The alloy may contain Ni at about 18 to about 27 wt % of the alloy, at about 19 to about 25 wt. % of the alloy, at about 18 to about 24 wt. % of the alloy, at about 21 to about 26 wt. % of the alloy, or any integer value range spanning 18 to 27 wt % of the alloy.

Other alloying additions, e.g., of total ternary, quaternary, quinary, and so forth alloying additions may be at about 2 to about 8 wt % of the alloy, about 2 to about 7 wt. % of the alloy, or any integer value range spanning 2 to 8 wt % of the alloy. The ternary or higher additions may comprise one or more of Ir, Pd, Rh, Ru, Nb, Mo, Re, W, Ta, or any combination thereof. For instance, in an alloy with a Re ternary addition, the Pt—Ni—Re alloy may contain about 21.8 wt. % Ni and about 72.4 wt. % Pt and about 5.8 wt. % Re. In another example, ternary or higher additions is present at about 2 to about 7 wt. % of the alloy, with Ni present at about 19 to about 25 wt. % of the alloy, with the balance being Pt.

In a platinum-rich alloy, platinum may be present at about 73 to about 80 wt. % of the alloy, nickel at about 18 to about 24 wt. % of the alloy, and total ternary or higher additions at about 2 to about 7 wt. % of the alloy. In a nickel-rich alloy, platinum may be present at about 68 to about 73 wt. % of the alloy, nickel at about 21 to about 26 wt. % of the alloy, and ternary or higher additions at about 2 to about 7 wt. % of the alloy.

In some implementations, the Pt—Ni—X alloy may be substantially free of one or more of Ti, V, Cr, Mn, Fe, Co, Cu, Zn, e.g., Period 4 transition metals except for Ni. Whereas in other implementations, the alloy may include an alloying addition of one or more of the aforementioned elements, such as Cu and/or Co. For instance, Cu and/or Co may replace a portion of the Ni in a quaternary alloy. In some implementations, the Pt—Ni—X alloy may include grain refiners such as Sc, Y, La series elements in amounts of 0.1 wt. % or less.

In other implementations the Pt—Ni—X alloy may contain nickel and platinum in a ratio such that Ni:Pt is in the range of about 1:2.4 to 1:4.5 by weight or preferably about 1:3.3 by weight. Ternary or higher order additions ("X") may include but are not limited to Ir, Pd, Rh, Ru, Nb, Mo, Re, W, Ta, or any combination of two or more of the foregoing. In addition to the ternary and higher compositions disclosed here there also exist in the alloys traces of other unnamed elements that are present not by intentional addition but through unavoidable tramp or impurity elements whose occurrence is familiar to those skilled in the art.

It has been discovered that for a wire formed of the Pt—Ni—X alloy of the present disclosure, the alloy can be formed and then subjected to age hardening, which surprisingly provides a significantly stronger wire. For instance, the alloy can be formed in an annealed state and then heat treated for age hardening. Depending on the desired properties, age hardening may be conducted, e.g., by heating in a furnace, usually under a mildly reducing or inert atmosphere, at times and temperatures ranging respectively from about 0.15 to 8 hours at temperatures from 400° F. to 1100° F. In a particular example, age hardening may be conducted for a maximum of about 8 hours while achieving the high strength alloy of the present disclosure. In one example, as a wire composed of the alloy is thermally aged, the strength of the wire may increase up to about 320 ksi to about 425 ksi. For instance, the Pt—Ni—X alloy can be age hardened to an ultimate tensile strength of at least 303 ksi, or at least 600 Vickers. Further, an age hardened alloy may have a microhardness of at least 580 Knoop. The age hardened alloy may have a total tensile elongation of greater than 1.5%.

The Pt—Ni—X alloy may be employed as a medical device spring, coil, or microcoil in the construction of a guidewire. The alloy and components made therefrom may be used in medical applications, such as percutaneous coronary intervention.

Implementations of the present disclosure may also involve Pt—Ni—X alloys in the testing of electronic device components. The alloy and components made therefrom may be used in the construction of test tools in forms such as such as wires, pins, needles, and other elements for the evaluation of electronic devices.

Application in Medical Devices

Guidewires are devices used in the course of percutaneous coronary intervention (PCI), as well as other intravascular procedures. Large-diameter guidewires are required to position the "introducer," the device which acts as a pathway from outside the body to the femoral artery during PCI. A narrower guidewire (the type of interest in the present disclosure) is subsequently passed through the introducer, through the vasculature, and to the opening of the coronary artery. The wire is then used to facilitate the placement of diagnostic catheters for radiopaque dye introduction, as well as guiding catheters for balloon angioplasty, and subsequently stent deployment.

Guidewires are understood to consist of the following primary components: a shaft, a core, a tip, a jacket, and a coating. For instance, FIG. 1 is an illustration of a catheter guidewire, which, at its distal tip, may contain a microcoil formed of an alloy of the present disclosure. Image adapted from Buller et al. (2013). The shaft is a solid wire typically comprising high-yield strength stainless steel. Typical diameter size is <0.015 inches, although shafts with a diameter as small as 0.009 inches are available. The shaft is responsible for transmitting torque during placement and facilitating the placement of transluminal catheters during the procedure. Kink resistance is critical in this component. The core is a tapered metallic component that is attached to the distal end of the shaft, typically with a length of 11 in. or more. Stainless steel or Nitinol may be used for the core material. Tapering of the core via conical or parabolic grinding allows the tip to conform to the tortuous vascular anatomy.

The transitional area from the guidewire core to distal end, or tip, the so-called "core-to-tip design," may involve a low-stiffness stainless steel ribbon, a second internal spring coil, or other contrivance. Microcoil outer diameter may be as small as 0.009 inches. Additionally, it is necessary for the tip assembly to comprise small diameter wires that maintain opacity to fluoroscopic level X-ray radiation in order to facilitate placement during PCI. An X-ray radiopaque marker may be attached to the tip of the device if the bulk of the core and tip comprises a poorly radiopaque material such as stainless steel.

A polymer over-coating or jacket may be used to improve the core-to-tip transition and reduce friction between the wire tip and surrounding tissues. Extensions of these jackets to form polymer-only tips (e.g., without a microcoil) have been tried, but with consequences to rotational and shape stability. A thin hydrophilic or hydrophobic coating is utilized to further modulate the device-tissue interaction. Hydrophilic coatings attract water, thus creating a uniform film of water and enhancing the lubriciousness of the tip during tissue contact. Hydrophobic coatings repel water and remain "slippery" without relying on water film formation.

According to certain implementations, the Pt—Ni—X alloys of the present disclosure may be formed as springs, coils or microcoils. For instance, the alloy may be a component of a medical device, such as a catheter guidewire where the spring, coil, or microcoil is arranged at the core or tip of the guidewire. When employed in the form of springs, coils, or microcoils a wire diameter of the Pt—Ni—X alloys of the present disclosure may be approximately 20-100 µm. The alloy may have a total tensile elongation of greater than 1.5%.

In some implementations as microcoils, the mechanical requirements of the Pt—Ni—X alloys of the present disclosure may require:
1). the material have sufficient stiffness to steer the guidewire through biological pathways, which is related to the elastic modulus, which may preferably be a high value, greater than about 2500 ksi, and/or
2). the material deflect slightly without deforming, which is related to elastic range (defined as the 0.2% offset yield strength divided by the Young's Modulus), and for instance may have a 0.2% offset yield strength of greater than 200 ksi, and/or
3). the elastic range be improved by increasing yield stress, conventionally by work hardening the material, not less than about 0.8%, and/or
4). the material has some minimum amount of ductility to prevent brittle fracture in application, not less than about 1.5% elongation to failure.

The Pt—Ni—X material may be in the form of a wire capable of being taken up from a spool. In some implementations the material may further be coiled into a spring, coil, and/or microcoil by a wire forming system. This may require:
1). a nominal level of straightness, which may preferably be a straightness of about 0.020 to about 0.025 inches of curvature per linear inch of length, and/or
2). a well-controlled springback behavior (equivalent to the material stress in forming divided by the elastic modulus), which may preferably be a low springback, not more than the equivalent elastic range of 0.6%, and/or
3). preferably high mechanical and chemical homogeneity, and/or
4). preferably high tensile elongation to failure, e.g., an elongation to failure of at least 1.5%.

Furthermore, chemical requirements of the Pt—Ni—X alloys of the present disclosure for application as certain medical device components may include:
1). the material be biocompatible and/or bioinert such that its use in an interventional or implantable medical device does not cause adverse reactions, and/or
2). the material be metallurgically compatible with components in the assembly to which it is welded, and/or
3). the material has high radiopacity to provide good X-ray fluoroscopic contrast, which may be achieved by the use of constituents of a high atomic number and/or high density.

For instance, the spring, coil, or microcoil may be configured such that when subjected to X-ray radiation at energies of about 40 to about 80 kV, it produces an X-ray image.

The Pt—Ni—X alloys of the present disclosure may be produced as guidewire tip components by:
1). drawing wire to the required diameter, introducing cold work,
2). straightening the wire by means of mechanical device (i.e. rotary wire straightening) or thermal treatment,
3). forming springs, coils, and/or microcoils from the straightened material, and
4). assembly of the component in a catheter guidewire, for example.

Alloys discussed in the present disclosure may be so employed in guidewire construction. However, due to the size and mechanical requirements of guidewire components, there is a fundamental conflict between the requirements to form a spring/coil/microcoil (low forming stress to provide low springback) and the function of the part, which incompatibly demands a high yield stress. This limits the strength of the wire that may be formed in to the spring. Such is the case for preceding usages of binary platinum-nickel alloys. U.S. Pat. No. 8,183,877 B2 (Tanaka 2012) instructs that platinum-nickel alloys may be worked by rolling through shaped grooves, by drawing at variable temperatures, and by drawing through dies into round wire. Accumulation of work in the material is used to provide strength and/or hardness; the material is "work hardened," or "wrought hardened."

In view of the foregoing conflict, it has been discovered that the Pt—Ni—X alloys of the present disclosure may be age hardened. This process provides both the desirable mechanical and the desirable chemical properties. Particularly, as described herein, the strength of the material comprising the spring may be significantly increased through age hardening. In some implementations, manufacture of a spring, coil, and/or microcoil comprising the Pt—Ni—X alloy of the present disclosure that is age hardened involves:
1). drawing wire to the required diameter, introducing cold work;
2). annealing the material to provide wire with a low forming stress/low springback, high wire straightness, and high elongation to failure;
3). manufacture of springs/coils/microcoils during which improved yields are realized due to the low spring back resulting from a lower yield strength after the anneal;
4). age hardening the material via subsequent thermal treatment to increase the yield strength and elastic range; and
5). assembly and deployment of the high-yield stress component in catheter guidewire or other application.

The combination of nobility, biocompatibility, wear-resistance, and elasticity possessed by the Pt—Ni—X alloys disclosed herein may further enable its application in other vascular medical devices. One example may include arterial and venal clot filters, which are typically constructed of wire that is formed into basket-like structures that filter blood flow. Another example would be in the form of embolic coils, where coils of wire are introduced into sites of vascular aneurism to form the requisite embolus and thus prevent later rupture. The ability of the Pt—Ni—X alloy of the present disclosure to be formed into very fine and flexible wires, springs, coils, and/or microcoils is a key characteristic for the efficient filling of the volume of the aneurysm. A further implementation may be as vascular ligating filaments or ligating clips.

Furthermore, certain orthopedic, musculoskeletal, maxillofacial, and/or craniofacial implants and devices may benefit from plates, wires, or fabricated components comprising the alloy of the present disclosure. The specific application should not carry a risk of stress shielding due to the high elastic modulus of platinum-based alloys relative to other orthopedic implant materials. Examples of appropriate applications may include sternal sutures, components of reconstructive plate-screw assemblies, and cranial reconstructive meshes. Alternatively, alloys of the present disclosure may be used in other types of orthopedic medical devices as X-ray opaque markers.

Application in Semiconductor Test

Alloys in test probes: Common amongst all electrical devices that require testing—including integrated circuits, packaging, and assemblies—is the constant decrease over time in physical form factor and dimension with concurrent increases in component, transistor, and/or power density. The function of such probes is to carry electrical impulse and signal from a piece of test equipment to test points on the device.

Due to the decreased pad area allotted to test points on electronic devices, probes may be required to have a smaller cross-section, yet still achieve a desired minimum contact force (or "gram force") required to achieve adequate electrical continuity after touchdown. The displacement may be controlled by means of vertical displacement, by means of a planned length of lateral displacement of the tip or "scrub length," or similar means against a gold, copper, aluminum, or similar pad material. Additionally, there are times where a tenacious, electrically insulating oxide present on the device test point must be physically disrupted to ensure electrical continuity. In these situations, probe alloys must possess high hardness to pierce the oxide and resist wear by abrasion. In the case of the evaluation of electronic packaging, the tip may sit on or cradle a solder bump comprising lead-based or lead-free solders of various compositions and their respective surface oxides. The marks made during touch-down on a device under test are subsequently used as means of quality control, to ensure the respective integrated circuit or electronics package has undergone the appropriate testing.

In some applications, wear-resistance of the probes employed in test is paramount. Removal of material from the test probe may occur via abrasive wear. In the case of wear in the abrasive mode, the tip of a test probe is worn away slowly in the form of metal fines or flakes. This occurs by interaction with test pads on the integrated circuit or electronic package, by devices used to clean or remove contaminants from the contact surface by means of abrasion, and other mechanical interactions.

In some of the same applications and others, the yield strength and ultimate tensile strength of the probes employed in test is paramount. This is due to deflection imposed on the probe so as to achieve a scrubbing or cleaning action on the contact area, referred to as "overdrive."

In some applications, resistance to environmental interaction of the probes employed in test is of high importance. Examples of these environmental interactions include resistance to tarnish or oxidation when elevated probe temperatures result from high test currents. In these applications the well-known noble nature of platinum and its alloys provide the required resistance to environmental effects.

The Pt—Ni—X alloy of the present disclosure may be included in test probes. For instance, the probe may be configured as a cobra probe, a cantilever probe, a pogo pin probe, a vertical probe, or a MEMS (micro-electro mechanical system) probe. The probe may additionally be a component of a probe card. The probe may be attached to a body comprising a dissimilar metal, which may be a component of probe cards. In some applications as electronic test device probes or probe components, the Pt—Ni—X alloy may be desired to possess the following mechanical attributes:

1). a microhardness of at least 600 Vickers;
2). high ultimate tensile strength, from about 320 ksi to about 425 ksi;
3). sufficient ductility to accommodate forming, denoted by at least 1.5% total elongation to failure; and/or In some implementations, the alloy may be age hardened and have the aforementioned mechanical attributes. For instance, the alloy may be a tensile strength of at least 320 ksi, and/or may have a microhardness of at least 600 Vickers, and/or may have a total tensile elongation of greater than 1.5%.

In some applications to ensure manufacturability as test device probes or components, a Pt—Ni—X alloy of the present invention may be required to possess one or more of the following attributes:

1). the ability to be drawn down to a diameter of about 15 µm (0.00059 inches);
2). in the form of wire, high straightness of about 0.002 inches of curvature per linear inch of length; and/or
3). in the form of rod, machinability into various shapes by means of techniques such as computer numerical control screw machining, surface grinding, electro discharge machining, or other similar techniques.

As stated, the performance of test probes for electronic devices is governed, in some cases, by the environmental interactions of the metal probe with the test substrate. For this reason, a Pt—Ni—X alloy of the present disclosure would be desired to contain greater than about 50 wt. % of noble metal, defined as a combination of platinum, and its group metals. The result is an enhanced resistance of the alloy to atmospheric contamination (i.e. oxidation, sulfidation, etc.) and to reaction with various process agents and contaminants to which a probe may be exposed in application.

Alloys and Their Behaviors

Figure 2:
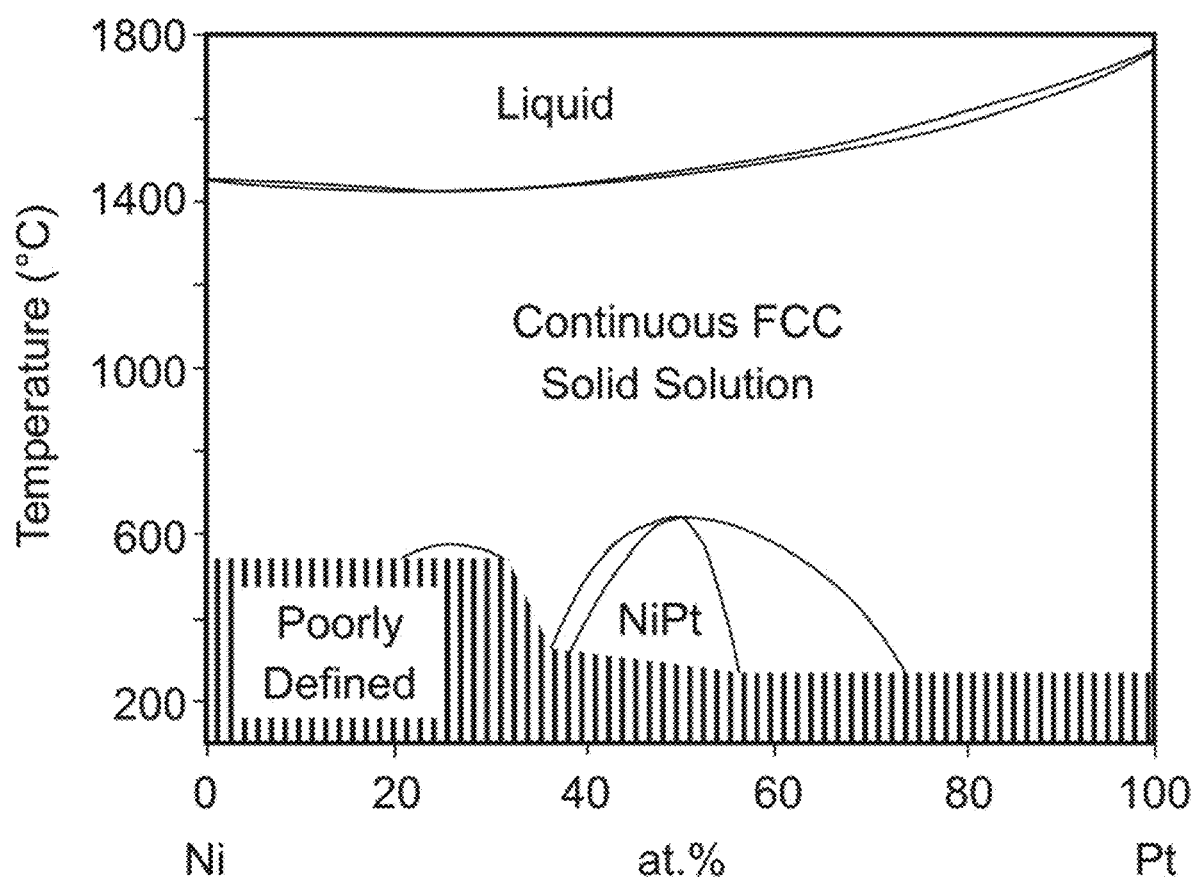
FIG. 2 illustrates a binary alloy phase diagram from ASM Alloy Phase Diagram Database for Ni—Pt, adapted from (Nash and Singleton 1991).

While not desiring to be bound by a particular theory, it is believed that age hardening of the Pt—Ni—X alloys of the present disclosure may be due to the material undergoing an ordering reaction during the age hardening heat treatment. The ordering reaction may provide an alloy with increased strength and may contribute to a lower level reactivity, making the product biocompatible. Material that is nominally equiatomic PtNi (50% Pt-50% Ni on an atomic basis) may undergo an ordering reaction that can serve to age harden the alloy, illustrated in FIG. 2. More particularly, FIG. 2 illustrates a binary alloy phase diagram from ASM Alloy Phase Diagram Database for Ni—Pt, adapted from Nash and Singleton (1991). Base compositional range that can provide the age hardening/ordering response of interest to form the PtNi phase includes at least about 42 at. % Pt up to about 58 at. % Pt, with the balance being Ni (or about 70.7 wt. % Pt up to about 82.1 wt. % Pt, with the balance Ni) per Dahmani et al. (Dahmani, Cadeville, and Pierron-Bohnes 1985).

The structure and kinetics associated with the NiPt ordering reaction have been studied for some decades. The work by Greenholz et al., for instance, uses X-ray diffraction to analyze the ordering of a Pt—Ni alloy (Greenholz, Kidron, and Shimony 1972), although in their experiments the ordering reaction proceeds over many tens of hours; e.g. 18-120 h at 900° F. In work by Greenberg (Greenberg et al. 2003), the stress-strain behavior of equiatomic NiPt was evaluated over a series of age hardening treatments up to 80 h. Ultimate tensile strengths roughly equivalent to those reported in U.S. Pat. No. 8,183,877B2 (Tanaka 2012) were found, with an effective maximum of 320 ksi.

Figure 3:
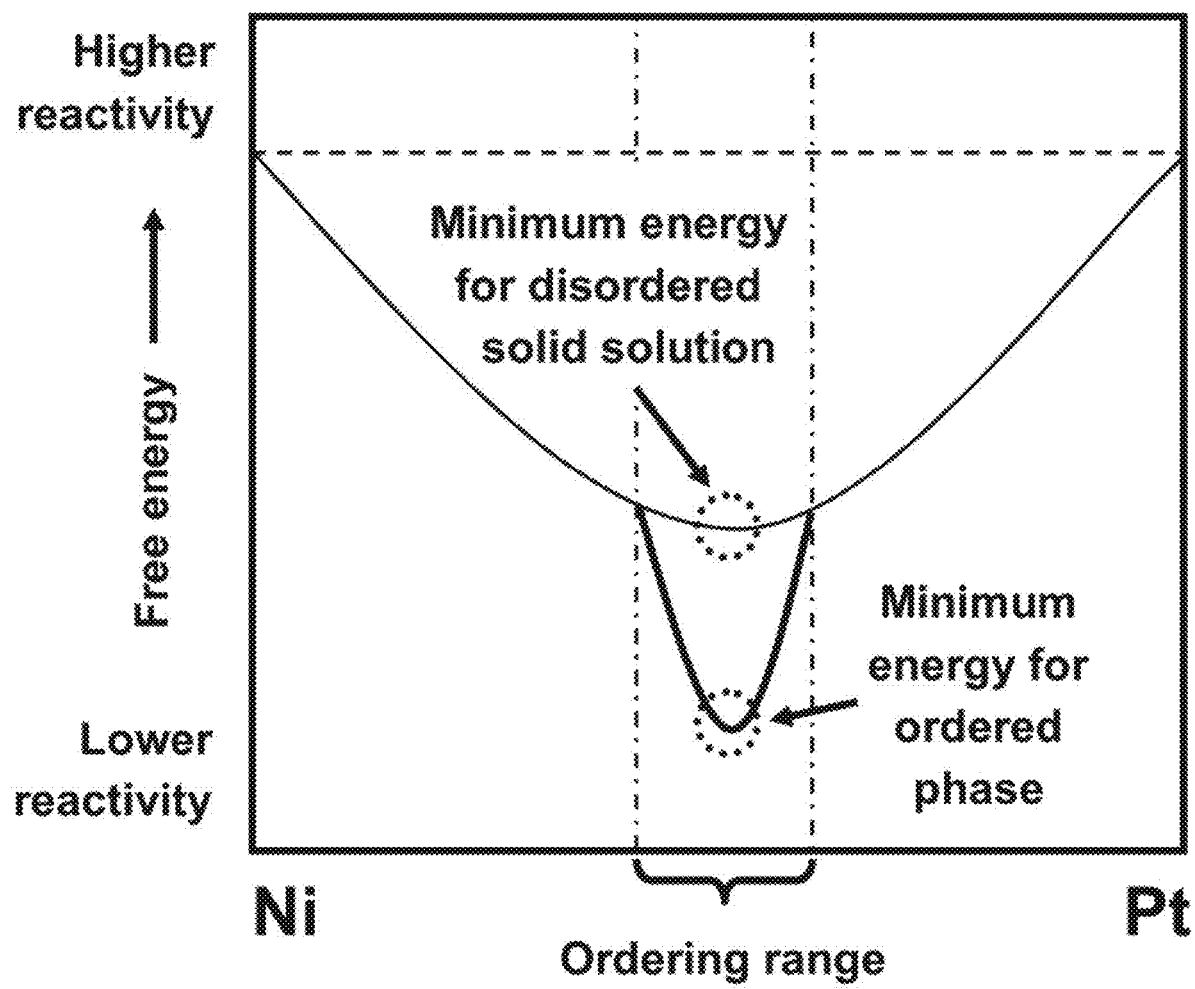
FIG. 3 illustrates a schematic representation of the free energy minimum associated with the structural ordering reaction in Pt—Ni.

While the proportion of platinum and its group metals in Pt—Ni—X alloys of the present disclosure is high, indicating proportionally high nobility, the aforementioned ordering reaction may have the unique potential to further reduce the chemical activity of the non-noble alloy constituents. While not desiring to be bound by a particular theory, it is believed that non-desirable chemical actors (i.e. Ni atoms in Pt—Ni—X) are more strongly bound to their atomic neighbors in the ordered state, and therefore less likely to be reactive with the surrounding environment. For example, ordered Pt—Co structures used in catalysis showed higher chemical stability in an ordered configuration, evident as "minimal loss of activity after 500 potential cycles on the ordered structure" according to Wang and (Wang et al. 2013). This minimum in free energy appears schematically as FIG. 3, which illustrates a schematic representation of the free energy minimum associated with the structural ordering reaction in Pt—Ni. If this behavior translates to Pt—Ni—X in a biological environment, then the ionic release of the Ni constituent and any non-noble ternary and higher constituents in the age hardened/ordered Pt—Ni—X alloy may be reduced relative to the same alloy in the disordered state.

Per the preceding mechanical and chemical requirements, a series of experimental materials were designed on the basis of atomic composition. Specific compositions and their observed processability are shown in Table 1. Preference was given to elements with high atomic number/high density with solubility in both Ni and Pt. Elements evaluated as ternary additions included Ag, Au, Pd, Re, W, Ir, Ta, and Ru.

An alloy of binary constitution, 76.87 wt. % Pt-23.13 Ni, consistent with the U.S. Pat. No. 8,183,877 B2 (Tanaka 2012) was also fabricated. This constitutes a comparative example, denoted "CE" in Table 1. The comparative example was processed as rod and wire, just as the numbered ternary and higher order alloys of the present disclosure were. It was found that the comparative example was processable into the form of rod/wire, as U.S. Pat. No. 8,183,877 B2 (Tanaka 2012) instructs.

All compositions of Pt—Ni—Ag or Pt—Ni—Ag—X—Alloys 2061-2069—were not processable to rod forms or to wire forms of sufficient quality. While not desiring to be bound by a particular theory, it is believed this poor processability is attributable to the phase separation of Ag from a matrix comprising Pt—Ni. The resultant microstructure may then contain two phases with vastly differing work hardening characteristics, thus decreasing the material's tolerance for deformation. These results indicate that Ag is to be avoided as an addition to Pt—Ni—X.

It was further observed, as shown in Table 1, that Alloys 2074 and 2075 (Pt—Ni—Au) were not processable, as they were observed to fail during the initial breakdown by gross cracking of the overwork type. This suggests that Au is not a reasonable addition to Pt—Ni—X in significant amounts due to resultant poor processability. This unexpected loss of processability due to Au content may not have been predicted solely on the basis of the binary alloy phase diagrams.

TABLE 1

Table of compositions evaluated and their ability to be processed into a wrought wire product.

| Alloy | Composition (wt. %) | | | | | | | | | | Processable? |
|---|---|---|---|---|---|---|---|---|---|---|---|
| | Pt | Ni | Ag | Au | Pd | Re | W | Ir | Ta | Ru | |
| 2061 | 73.58 | 22.14 | 4.28 | — | — | — | — | — | — | — | N |
| 2062 | 70.24 | 21.13 | 8.63 | — | — | — | — | — | — | — | N |
| 2063 | 63.40 | 19.07 | 17.53 | — | — | — | — | — | — | — | N |
| 2064 | 52.73 | 15.87 | 31.40 | — | — | — | — | — | — | — | N |
| 2065 | 41.55 | 12.50 | 45.95 | — | — | — | — | — | — | — | N |
| 2066 | 69.07 | 20.78 | 8.58 | 1.57 | — | — | — | — | — | — | N |
| 2067 | 64.53 | 19.41 | 8.40 | 7.66 | — | — | — | — | — | — | N |
| 2068 | 69.57 | 20.93 | 8.64 | — | 0.86 | — | — | — | — | — | N |
| 2069 | 66.88 | 20.12 | 8.70 | — | 4.30 | — | — | — | — | — | N |
| 2072 | 72.44 | 21.80 | — | — | — | 5.76 | — | — | — | — | Y |
| 2073 | 68.18 | 20.50 | — | — | — | 11.32 | — | — | — | — | Y |
| 2074 | 72.20 | 21.72 | — | 6.08 | — | — | — | — | — | — | N |
| 2075 | 67.73 | 20.38 | — | 11.89 | — | — | — | — | — | — | N |
| 2076 | 72.50 | 21.81 | — | — | — | — | 5.69 | — | — | — | Y |
| 2078 | 70.29 | 21.15 | — | — | 8.56 | — | — | — | — | — | N |
| 2079 | 76.06 | 21.09 | — | — | 2.85 | — | — | — | — | — | Y |
| 2080 | 73.15 | 23.88 | — | — | 2.97 | — | — | — | — | — | Y |
| 2081 | 70.36 | 21.17 | — | — | — | — | 8.47 | — | — | — | N |
| 2082 | 76.09 | 21.10 | — | — | — | 2.81 | — | — | — | — | Y |
| 2083 | 73.18 | 23.89 | — | — | — | 2.93 | — | — | — | — | Y |
| 2087 | 71.36 | 21.47 | — | — | — | 7.17 | — | — | — | — | N |
| 2088 | 71.59 | 25.37 | — | — | — | 3.04 | — | — | — | — | Y |
| 2089 | 77.43 | 19.78 | — | — | — | 2.79 | — | — | — | — | Y |
| 2090 | 69.33 | 24.66 | — | — | — | 6.01 | — | — | — | — | Y |
| 2091 | 70.92 | 23.20 | — | — | — | 5.88 | — | — | — | — | Y |
| 2092 | 73.90 | 20.46 | — | — | — | 5.64 | — | — | — | — | Y |
| 2093 | 75.30 | 19.17 | — | — | — | 5.53 | — | — | — | — | Y |
| 2094 | 72.30 | 21.76 | — | — | — | — | — | 5.94 | — | — | Y |
| 2095 | 72.56 | 21.84 | — | — | — | — | — | — | 5.60 | — | N |
| 2096 | 74.40 | 22.40 | — | — | — | — | — | — | — | 3.20 | Y |
| CE | 76.87 | 23.13 | — | — | — | — | — | — | — | — | Y |

Alloy 2095 was observed to break at intermediate diameters during rotary hammer swaging, suggesting that the material as alloyed was capable of limited plastic deformation, and further suggesting that an addition less than about 5.6 wt. % Ta may improve processability. This unexpected limit on Ta content was not predicted solely on the basis of the binary alloy phase diagrams.

Alloys 2073, 2078, 2081, and 2087 did not survive through intermediate drawing, failing apparently as a result of center bursting. This may indicate that drastic work hardening behavior takes place during deformation of these materials, and additions greater than 7 wt. % of Re and W alone are considered unprocessable.

The balance of compositions were successfully drawn into the form of wire.

Figure 4:
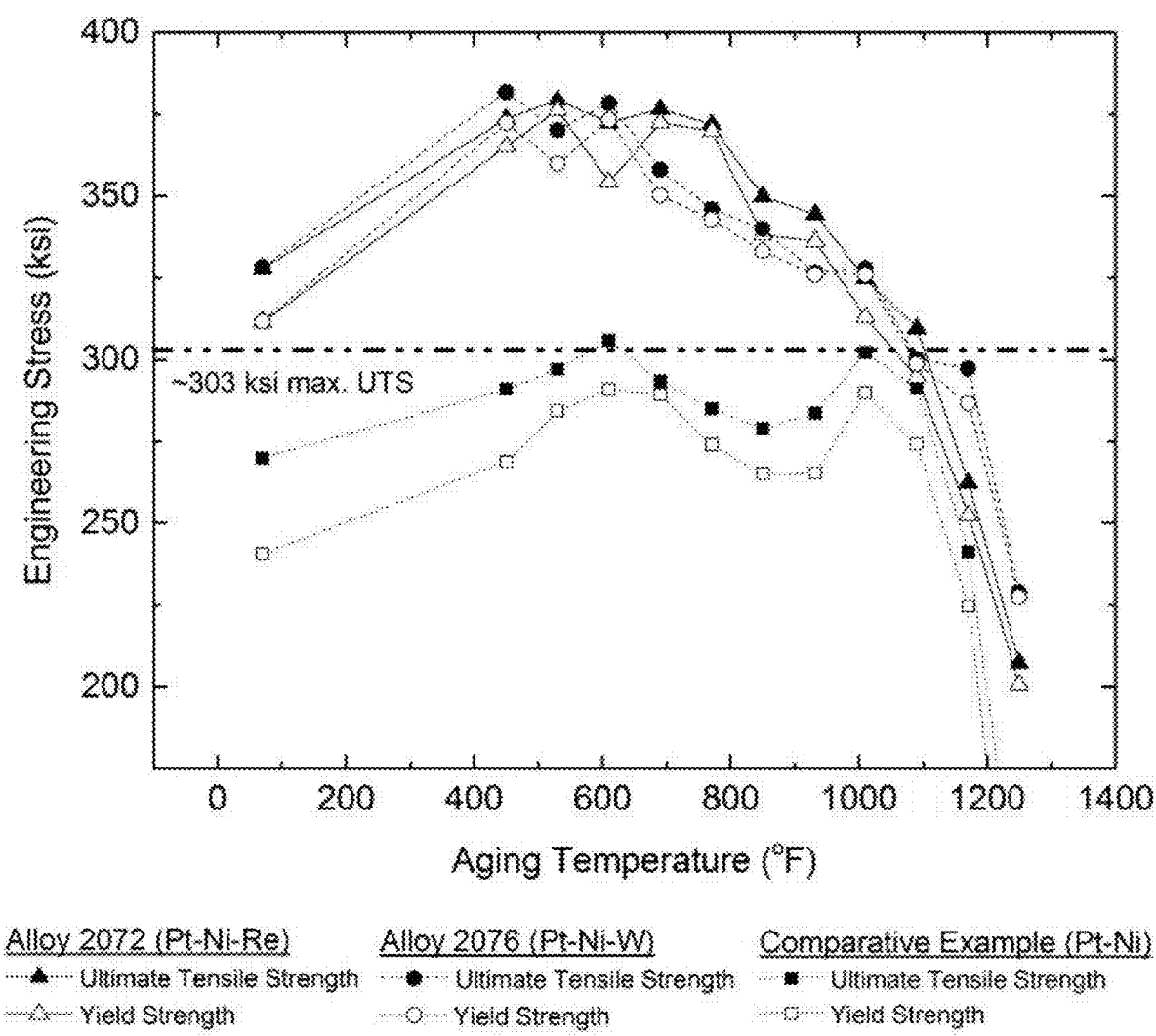
FIG. 4 illustrates a Pt—Ni—W (Alloy 2076) and a Pt—Ni—Re (Alloy 2072) isochronal 2-hour aging curve, strength measurements in monotonic tension, with yield strength shown as open markers, ultimate tensile strength shown as closed markers. Age hardening behavior of a binary platinum-nickel alloy is presented in the same fashion as a comparative example.
Figure 5:
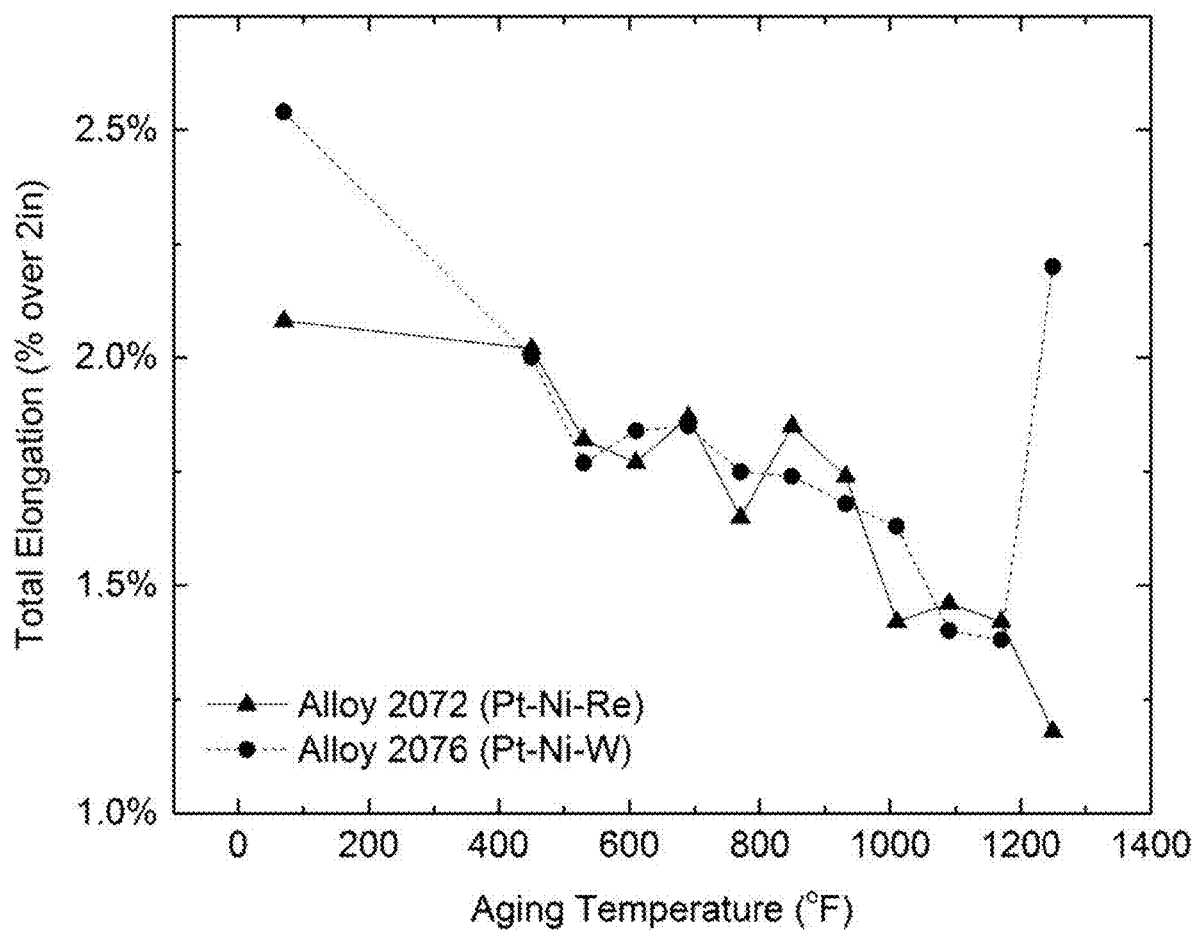
FIG. 5 illustrates a Pt—Ni—W (Alloy 2076) and a Pt—Ni—Re (Alloy 2072) isochronal 2-hour aging curve, elongation to failure in monotonic tension.

Following the drawing of Alloys 2072 and 2076 to 0.0025 in diameter wire, extensive experiments were performed on the resultant materials. An isochronal aging curve (2 h constant time) was produced by aging materials at a range of temperatures. The observed material strengths are presented in FIG. 4, and elongations in FIG. 5. FIG. 4 illustrates a Pt—Ni—W (Alloy 2076) and a Pt—Ni—Re (Alloy 2072) isochronal 2-hour aging curve, strength measurements in monotonic tension, with yield strength shown as open markers, ultimate tensile strength shown as closed markers. Strength values in monotonic tension were also acquired for the Pt—Ni comparative example, abbreviated "CE" in FIG. 4. It is observed that very high material ultimate tensile strengths, greater than 350 ksi, are reached at aging temperatures between roughly 250° F. and 900° F. in the ternary alloys (Pt—Ni—Re and Pt—Ni—W alloys). This should be contrasted with the comparatively lower ultimate tensile strengths of the binary comparative example alloy, which achieved a maximum ultimate tensile strength of 305 ksi over the same aging treatments. This maximum observed strength for the comparative example is very close to the 303 ksi strength value (equivalent to maximum HV 600 hardness) claimed by U.S. Pat. No. 8,183,877 B2 (Tanaka 2012). FIG. 5 illustrates a Pt—Ni—W (Alloy 2076) and a Pt—Ni—Re (Alloy 2072) isochronal 2-hour aging curve, elongation to failure in monotonic tension. In regards to elongation, cold worked and near-peak aged materials (2 h at <1000° F.) meet the criterion of >1.5% elongation to failure. Microhardness measurements were also performed by mounting samples in 2-part epoxy, polishing in cross section to a mirror finish, and utilizing a Knoop hardness indenter system at 50 $g_f$ load with five indents averaged per sample. Microhardness measurements presented in FIG. 6, which illustrates a Pt—Ni—W (Alloy 2076) and a Pt—Ni—Re (Alloy 2072) isochronal 2-hour aging curve, Knoop hardness (50 $g_f$) measurements on longitudinal cross-section. Hardness values for cold worked and most aged conditions are in excess of $HK_{50}$ 550, and many are in excess of $HK_{50}$ 600.

Figure 6:
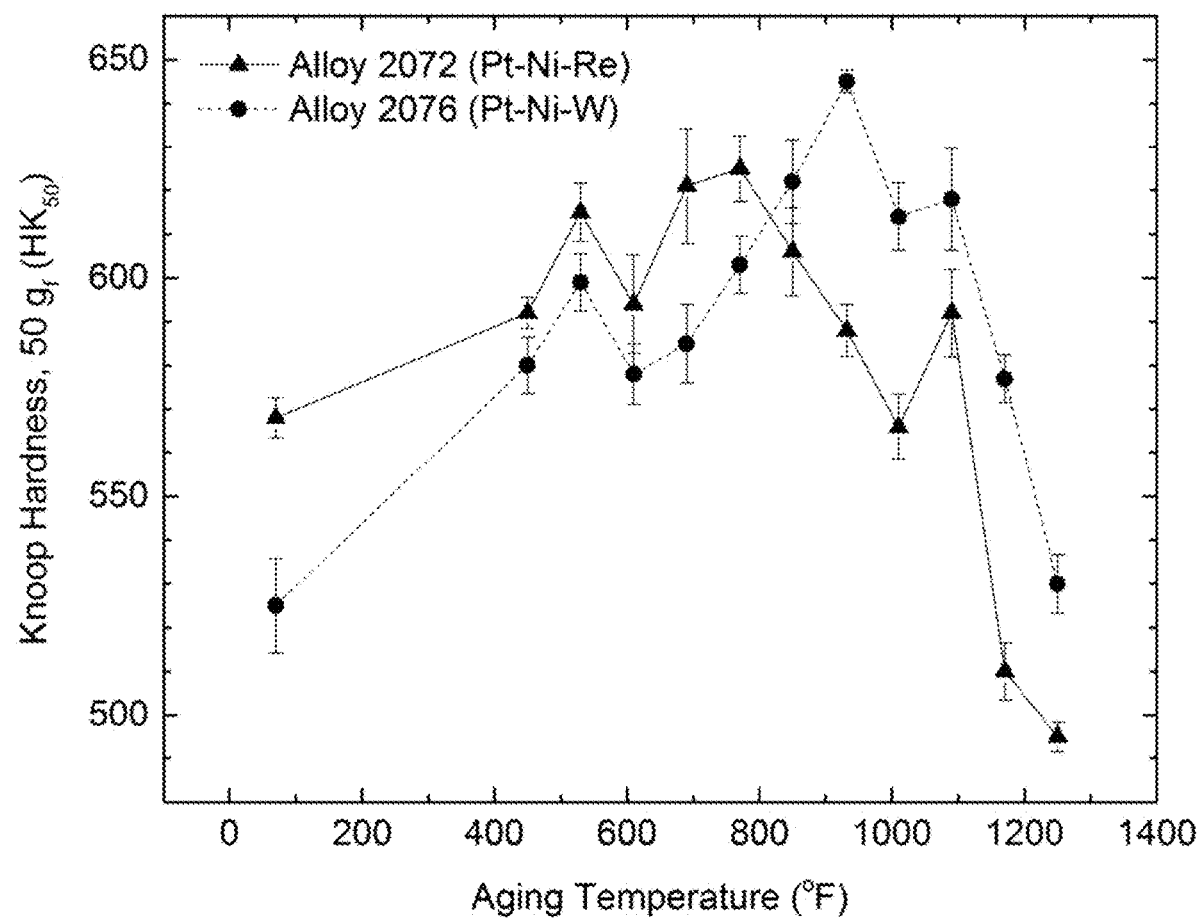
FIG. 6 illustrates a Pt—Ni—W (Alloy 2076) and a Pt—Ni—Re (Alloy 2072) isochronal 2-hour aging curve, Knoop hardness (50 $g_f$) measurements on longitudinal cross-section.

High strength is classically associated with high hardness and/or microhardness, as both are fundamentally tied to the material's resistance to plastic deformation. Surprisingly, this does not appear to be the case for some Pt—Ni—X materials. This may be observed by comparing trends in microhardness (FIG. 6) with ultimate tensile strength (FIG. 4), both following a cold reduction in area of 90%. It is evident from FIG. 4 that a maximum ultimate tensile strength is reached by Alloy 2076 with an age hardening treatment of 2 hours at about 400-625° F., at a magnitude of approximately 365-385 ksi. In contrast, FIG. 6 illustrates that a maximum value of Knoop microhardness is reached by Alloy 2076 at the very different age hardening treatment of 2 hours at about 900-950° F., achieving a magnitude of about HK 640-650.

Another surprising outcome from this evaluation is the drastic age hardening that can be achieved in compositions of the present disclosure in as little as two hours, whereas literature suggests tens of hours of aging would be required for crystallographic ordering to occur (Greenholz, Kidron, and Shimony 1972).

Figure 7:
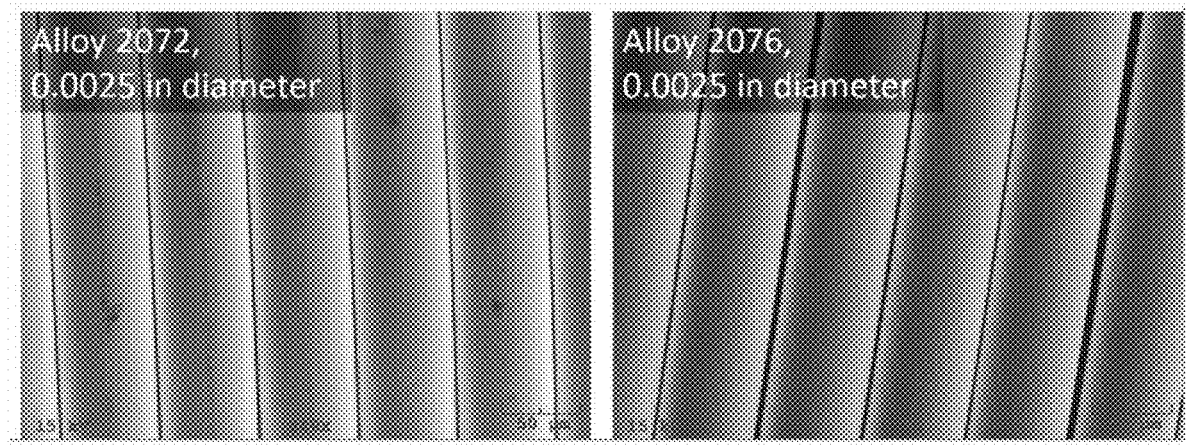
FIG. 7 is a SEM image of a coil inspection applied to 0.0025 in diameter wire coils of Pt—Ni—W (Alloy 2076) and Pt—Ni—Re (Alloy 2072).

Both Alloys 2072 and 2076 at the final size of 0.0025 in diameter underwent evaluation for surface quality by a scanning electron microscopy. A "coil inspection" method was utilized. In this protocol, material is wound into a helix thereby dramatically increasing the surface tensile stresses, thus magnifying any defects during inspection. The helical geometry also increases the length of wire available for review. After coiling, the samples were examined using the scanning electron microscope for evidence of surface defects (seams, slivers, draw lines, etc.). The material passed this inspection, and no indications of defects due to poor processability were observed, as evidenced by FIG. 7, which is a SEM image of a coil inspection applied to 0.0025 in diameter wire coils of Pt—Ni—W (Alloy 2076) and Pt—Ni—Re (Alloy 2072). This confirms manufacturability of materials at surprisingly high levels of microhardness, above 600 Vickers, in contrast to the teachings of U.S. Pat. No. 8,183,877 B2 (Tanaka 2012).

Figure 8:
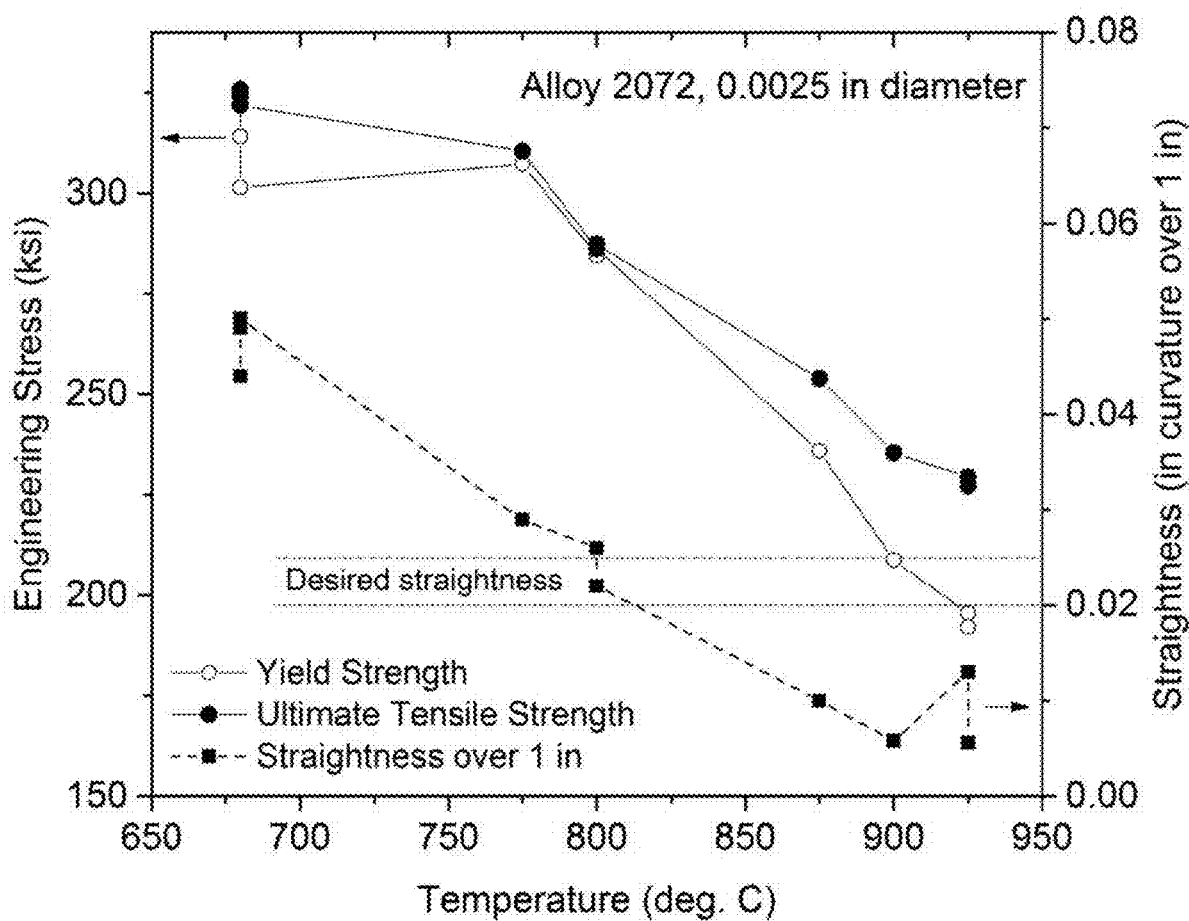
FIG. 8 illustrates an annealing curve for Pt—Ni—Re (Alloy 2072) at 0.0025 in diameter after 96% cold work. Strengths are shown with circular markers (UTS—closed markers, YS—open markers), and straightness over 1 in. is shown with square markers. The horizontal lines are references for straightness.
Figure 9:
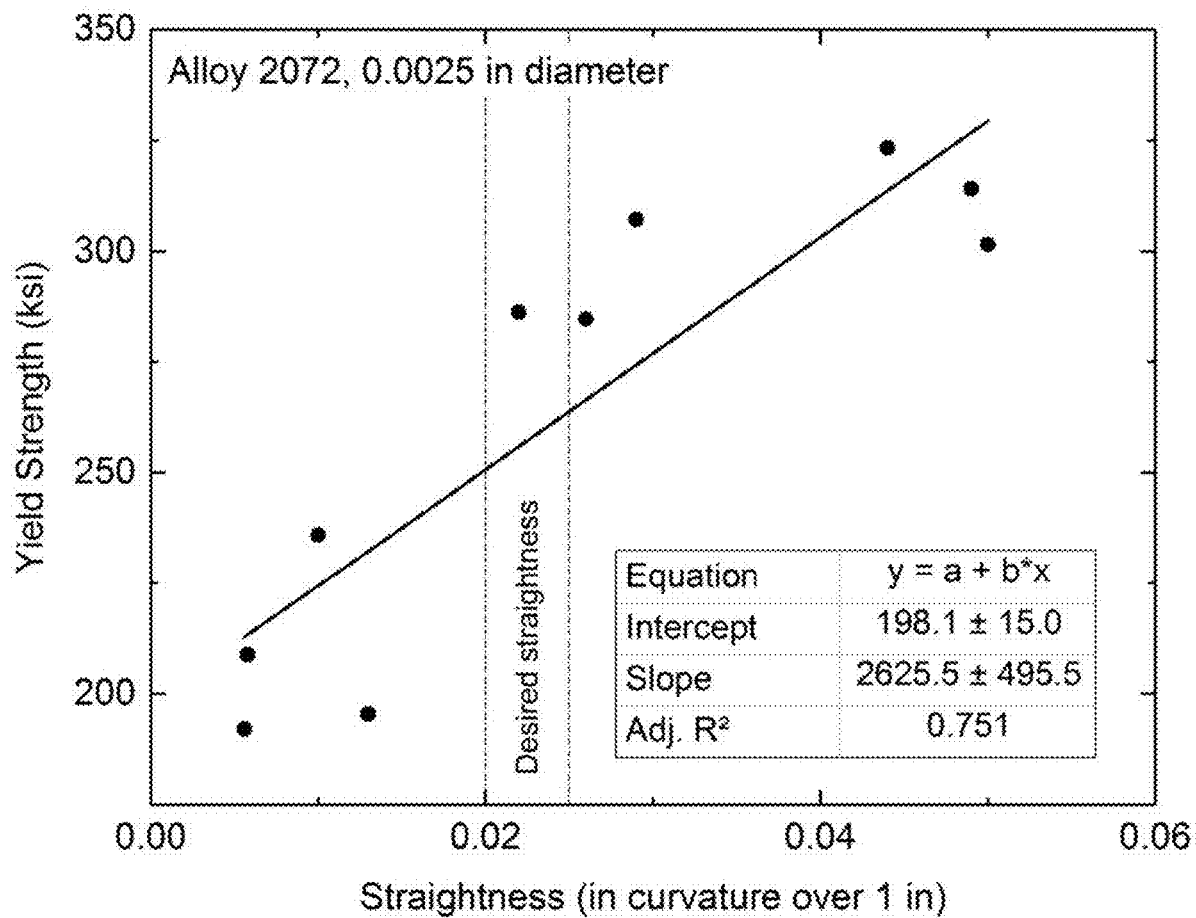
FIG. 9 illustrates a linear regression analysis of yield strength-straightness trade-off for Pt—Ni—Re (Alloy 2072) at 0.0025 in diameter after 96% cold work, where a degree of linearity is high ($R^2=0.75$). The solid vertical lines correspond to reference straightness values.

A curve of both straightness (expressed as inches of curvature over one linear inch of wire length) and yield and ultimate tensile strengths was constructed. FIG. 8 illustrates an annealing curve for Pt—Ni—Re (Alloy 2072) at 0.0025 in diameter after 96% cold work. Strengths are shown with circular markers (UTS—closed markers, YS—open markers), and straightness over 1 in. is shown with square markers. The set of horizontal lines is a reference for desired straightness. An inverse linear relationship was observed between strength in monotonic tension and material straightness, shown in FIG. 9. FIG. 9 illustrates a linear regression analysis of yield strength-straightness trade-off where a degree of linearity is high ($R^2$=0.75). The solid vertical lines correspond to the reference straightness values. The material is capable of achieving desired product straightness while retaining a high ultimate tensile strength in excess of about 240 ksi or in excess of about 250 ksi and a high 0.2% offset yield stress in excess of greater than 175 ksi, such as about 200 ksi. In some implementations, the alloy is annealed to a straightness of better than about 0.030 in. curvature per linear inch of length of wire and maintains an ultimate tensile strength of about 240 ksi or greater.

These desired annealed strengths of alloys of the present disclosure are similar in magnitude to the highly cold worked properties of the comparative example. This close relation strongly suggests that binary Pt—Ni materials may not be capable of achieving simultaneous straightness and high strength.

Measurements of X-ray radiopacity at a range of energies commonly used in chest X-ray (45-75 kV) were performed on samples of 89.5 wt. % Pt-10.5 wt. % Ni, 90 wt. % Pt-10 wt. % Ir, the comparative example, and Pt—Ni—X Alloys 2072 through 2076. X-ray imaging was performed atop an aluminum plate, or "phantom," intended to simulate the human chest cavity. A series of captured images from all aforementioned compositions are presented in FIG. 10, which is a compilation of X-ray radiopacity images from standard Pt—Ni and Pt—Ir and experimental Pt—Ni—Re, —Au, and —W experimental alloys. Following the acquisition of the X-ray images, quantification of radiopacity was performed by using image analysis. Grayscale values (0=black, 255=white) were acquired for each material and its adjacent phantom in each image along a selected line. These differences were then plotted as a simple function of accelerating voltage, as well as a value normalized to the 89.5 wt. % Pt-10.5 wt. % Ni image. The quantified results are presented in FIGS. 10 and 11. FIGS. 11A-B illustrates graphs of a quantification of X-ray radiopacity results from FIG. 10, corresponding to standard 89.5 wt. % Pt-10.5 wt. % Ni and Pt—Ir, the comparative example, and experimental Pt—Ni—Re, —Au, and —W experimental alloys. A larger difference in grayscale value indicates a higher X-ray attenuation, and therefore a higher radiopacity. An X-ray radiopacity nominally similar to the reference 89.5 wt. % Pt—10.5 wt. % Ni material is desirable for application as a spring, coil, or microcoil.

Figure 10:
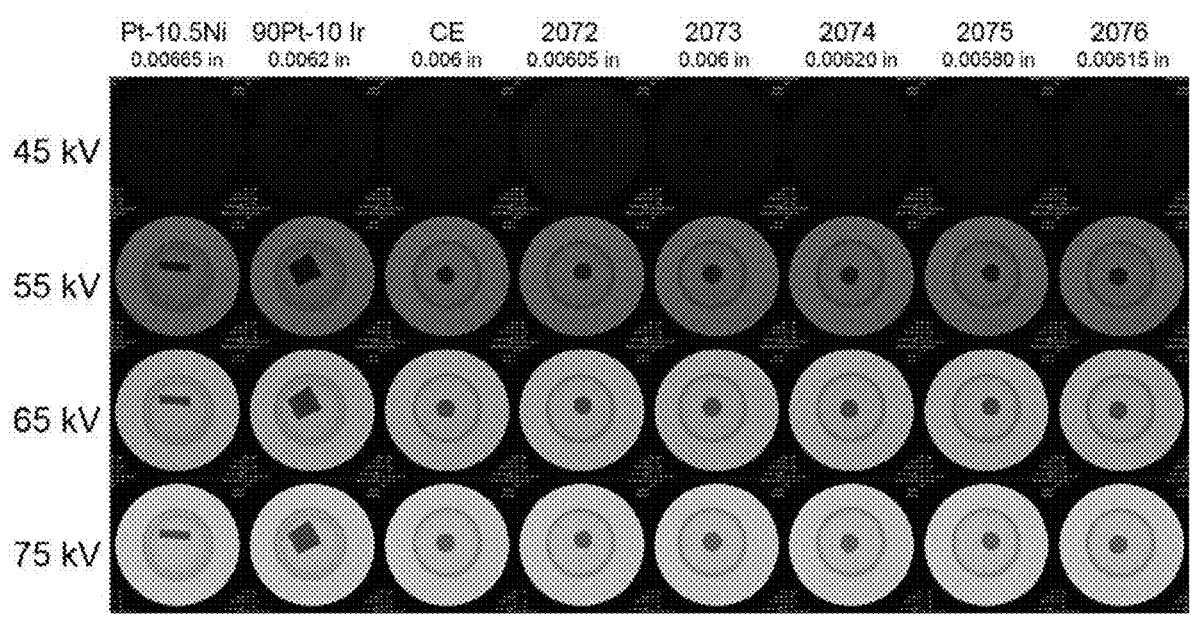
FIG. 10 is a compilation of X-ray radiopacity images from standard Pt—Ni and Pt—Ir materials; the Pt—Ni comparative example alloy; and experimental Pt—Ni—Re, —Au, and —W experimental alloys.
Figure 11A:
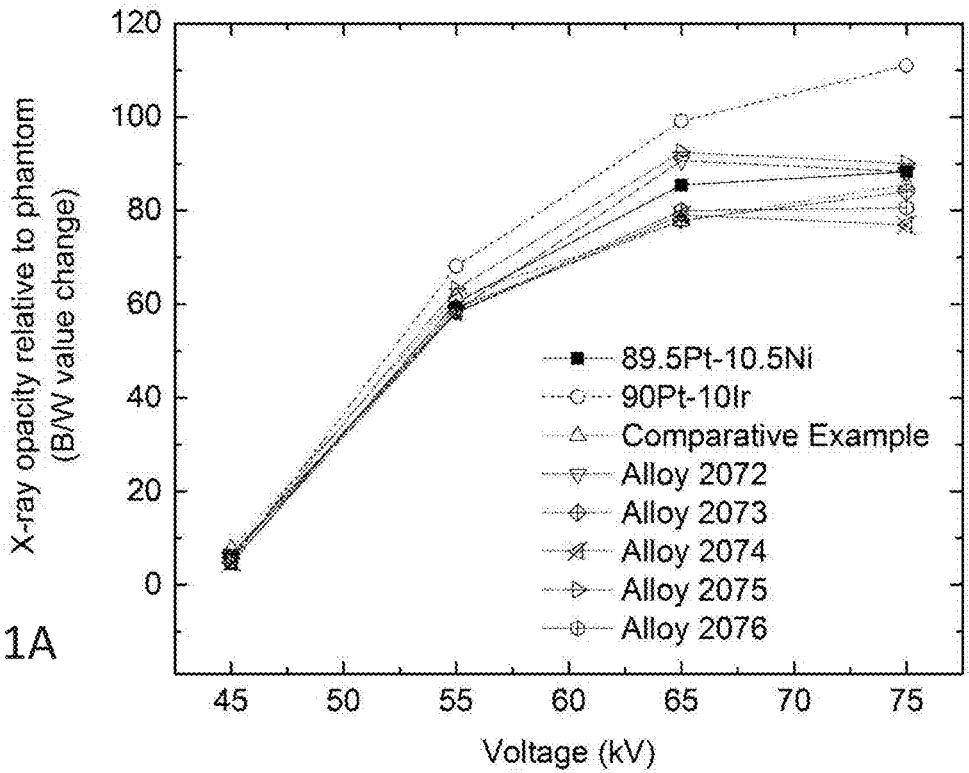
FIGS. 11A-11B illustrates a graph of a quantification of X-ray radiopacity results from FIG. 10, corresponding to standard Pt—Ni and Pt—Ir and experimental Pt—Ni—Re, —Au, and —W experimental alloys.
Figure 11B:
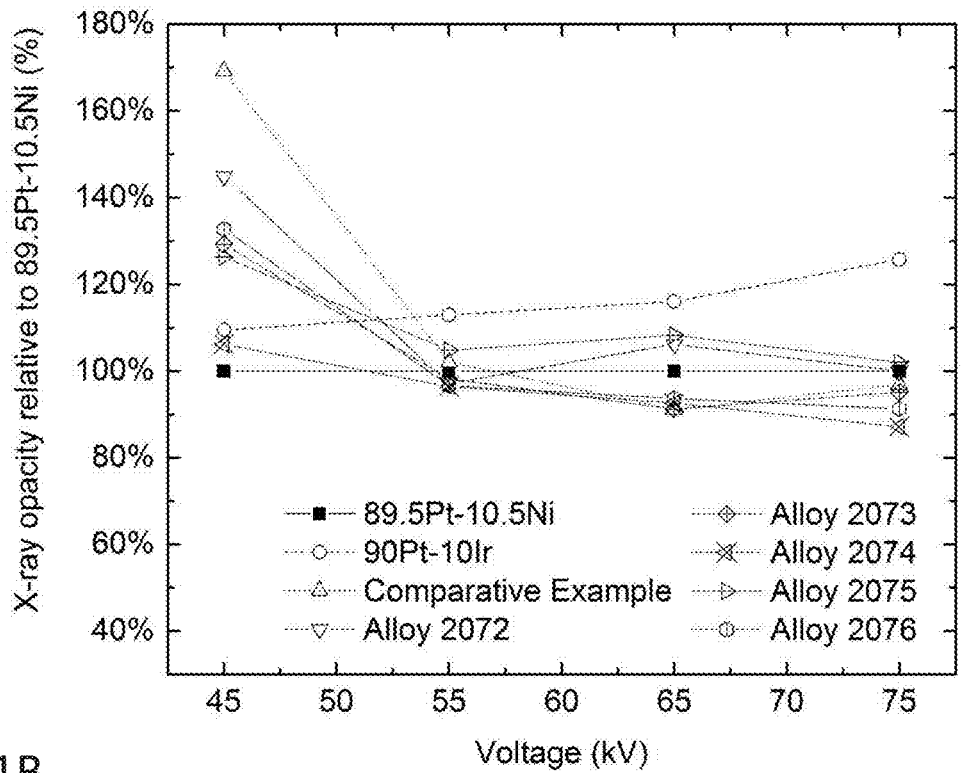

FIGS. 10 and 11A-11B suggest that the radiopacities of all the tested materials are very similar, all within about 15%, of the reference 89.5 wt. % Pt-10.5 wt. % Ni material. This is surprising due to the proportionally higher content of Ni in the Pt—Ni—X compositions of the present disclosure, which would be expected to substantially decrease the X-ray radiopacity. Unsurprisingly, experimental materials as well as the 89.5 wt. % Pt-10.5 wt. % Ni reference exhibited substantially lower X-ray radiopacity than 90 wt. % Pt-10 wt. % Ir at all voltages>55 kV, due to the relatively higher density and atomic number of Ir in comparison to Ni.

For medical applications, it is important to maintain biocompatibility. Therefore for these applications, the alloy should be essentially free of metals that may not be biocompatible; e.g., lead, mercury, cadmium, mercury, bismuth, tin, manganese, aluminum, antimony, osmium, and actinide series metals. Additionally, to maintain biocompatibility throughout fabrication, RoHS objectionable materials, such as hexavalent chromium ($Cr^{6+}$), polybrominated biphenyls (PBB), polybrominated diphenyl ether (PBDE), bis(2-ethylhexyl), phthalate (DEHP), butyl benzyl phthalate (BBP), dibutyl phthalate (DBP), and diisobutyl phthalate (DIBP), should not be used in the production of the medical grade versions of the Pt—Ni—X alloys of the present disclosure.

The term "substantially free" encompasses trace amounts of components that do not otherwise affect the material properties of the alloy. From the above description and drawings, it will be understood by those of ordinary skill in the art that the particular embodiments shown and described are for purposes of illustration only and are not intended to limit the scope of the present invention. Those of ordinary skill in the art will recognize that the present invention may be embodied in other specific forms without departing from its spirit or essential characteristics. References to details of particular embodiments are not intended to limit the scope of the invention.

What is claimed is:

1. A platinum and nickel-based ternary or higher alloy comprising:
   a) platinum at about 65 to about 80 wt. % of the alloy;
   b) nickel at about 18 to about 27 wt. % of the alloy; and
   c) a ternary or higher addition totaling about 2 to about 8 wt. % of the alloy, wherein the ternary or higher additions comprise one or more of Ir, Pd, Rh, Ru, Nb, Mo, Re, W, Ta, or any combination thereof,
   wherein the alloy is at least one of:
      annealed to a straightness of better than about 0.030 in. curvature per linear inch of length of wire and maintains an ultimate tensile strength of about 240 ksi or greater; or
      age hardened.

2. The alloy of claim 1, wherein nickel is present at about 19 to about 25 wt. % of the alloy, the total ternary or higher additions is present at about 2 to about 7 wt. % of the alloy.

3. The alloy of claim 1, wherein the platinum is present at about 73 to about 80 wt. % of the alloy, the nickel is present at about 18 to about 24 wt. % of the alloy, and the total ternary or higher addition is present at about 2 to about 7 wt. % of the alloy.

4. The alloy of claim 1, wherein the platinum is present at about 68 to about 73 wt. % of the alloy, the nickel is present at about 21 to about 26 wt. % of the alloy, and the ternary or higher additions are present at about 2 to about 7 wt. % of the alloy.

5. The alloy of claim 1, wherein the alloy is substantially free of Ti, V, Cr, Mn, Fe, Co, Cu, and/or Zn.

6. The alloy of claim 1, wherein the alloy comprises scandium, yttrium, or lanthanide in amounts of 0.1 wt. % or less.

7. The alloy of claim 1, wherein the alloy is annealed to the straightness of better than about 0.030 in. curvature per linear inch of length of wire and maintains the ultimate tensile strength of about 240 ksi or greater.

8. The alloy of claim 1, wherein the alloy is age hardened and has a microhardness of at least 580 Knoop.

9. The alloy of claim 1, wherein the alloy is age hardened and has an ultimate tensile strength of at least 320 ksi.

10. The alloy of claim 1, wherein the alloy is age hardened and has a total tensile elongation of greater than 1.5%.

11. A spring, coil, or microcoil product comprising a platinum-nickel-based ternary or higher alloy, the alloy comprising:
   a) platinum at about 65 to about 80 wt. % of the alloy;
   b) nickel at about 18 to about 27 wt. % of the alloy; and
   c) a ternary or higher addition totaling about 2 to about 8 wt. % of the alloy, wherein the ternary or higher additions comprise one or more of Ir, Pd, Rh, Ru, Nb, Mo, Re, W, Ta, or any combination thereof,
   wherein the product is a component of a guidewire comprising a core and/or tip utilizing the product.

12. The product of claim 11, wherein the spring, coil, or microcoil is subjected to X-ray radiation at energies of about 40 to about 80 kV and used to produce an image in a medical setting.

13. The product of claim 11, wherein the alloy has a total tensile elongation of greater than 1.5%.

14. The product of claim 11, wherein the alloy has a 0.2% offset yield strength of greater than 175 ksi.

15. The product of claim 11, wherein the alloy is at least one of:
   annealed to a straightness of better than about 0.030 in. curvature per linear inch of length of wire and maintains an ultimate tensile strength of about 240 ksi or greater; or
   age hardened.

16. A test probe comprising a platinum-nickel-based ternary or higher alloy, the alloy comprising:
   a) platinum at about 65 to about 80 wt. % of the alloy;
   b) nickel at about 18 to about 27 wt. % of the alloy; and
   c) a ternary or higher addition totaling about 2 to about 8 wt. % of the alloy, wherein the ternary or higher additions comprise one or more of Ir, Pd, Rh, Ru, Nb, Mo, Re, W, Ta, or any combination thereof,
   wherein the alloy is at least one of:
      annealed to a straightness of better than about 0.030 in. curvature per linear inch of length of wire and maintains an ultimate tensile strength of about 240 ksi or greater; or
      age hardened.

17. The test probe of claim 16, wherein the probe is configured as a cobra probe, a cantilever probe, a pogo pin probe, a vertical probe, or a MEMS probe.

18. The test probe of claim 16, wherein the alloy is age hardened and has a microhardness of at least 600 Vickers.

19. The test probe of claim 16, wherein the alloy is age hardened and has a tensile strength of at least 320 ksi.

20. The test probe of claim 16, wherein the alloy is age hardened and has a total tensile elongation of greater than 1.5%.

21. A probe card comprising the test probe according to claim 16.

22. The test probe of claim 16, wherein a tip made of the platinum-nickel-based ternary or higher alloy is attached to a body comprising a dissimilar metal.

23. A probe card comprising the test probe according to claim 22.

24. A method of producing a platinum and nickel-based ternary or higher alloy, the method comprising:
   a) forming an alloy comprising
      i) platinum at about 65 to about 80 wt. % of the alloy;
      ii) nickel at about 18 to about 27 wt. % of the alloy; and
      iii) a ternary or higher addition totaling about 2 to about 8 wt. % of the alloy, wherein the ternary or higher additions comprise one or more of Ir, Pd, Rh, Ru, Nb, Mo, Re, W, Ta, or any combination thereof;
   b) annealing the alloy;
   c) forming the annealed alloy into a probe tip, a spring, a coil, or a microcoil; and
   d) age hardening the formed, annealed alloy for a maximum of 8 hours,
wherein the alloy can be age hardened to an ultimate tensile strength of at least 320 ksi or at least $HK_{50}$ 600.

* * * * *